United States Patent
Young et al.

(10) Patent No.: US 11,375,969 B2
(45) Date of Patent: Jul. 5, 2022

(54) X-RAY APPARATUS HAVING A COMPOSITE FIELD OF VIEW

(71) Applicant: KONINKLIJKE PHILIPS N.V., Eindhoven (NL)

(72) Inventors: Stewart Young, Hamburg (DE); Daniel Bystrov, Hamburg (DE); Jens Von Berg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 18 days.

(21) Appl. No.: 16/469,679

(22) PCT Filed: Dec. 12, 2017

(86) PCT No.: PCT/EP2017/082444
§ 371 (c)(1),
(2) Date: Jun. 14, 2019

(87) PCT Pub. No.: WO2018/108923
PCT Pub. Date: Jun. 21, 2018

(65) Prior Publication Data
US 2020/0008768 A1 Jan. 9, 2020

(30) Foreign Application Priority Data
Dec. 15, 2016 (EP) .................................... 16204204

(51) Int. Cl.
*A61B 6/00* (2006.01)
*G06T 7/00* (2017.01)
(52) U.S. Cl.
CPC .......... *A61B 6/5241* (2013.01); *G06T 7/0014* (2013.01); *G06T 2207/10116* (2013.01);
(Continued)
(58) Field of Classification Search
None
See application file for complete search history.

(56) References Cited

U.S. PATENT DOCUMENTS

| 2009/0245464 | A1 | 10/2009 | Yamaguchi |
| 2015/0110245 | A1* | 4/2015 | Kim ..................... A61B 6/5241 378/62 |
| 2015/0228071 | A1 | 8/2015 | Jockel |

FOREIGN PATENT DOCUMENTS

| EP | 2767236 A1 | 8/2014 |
| EP | 2944260 A1 | 11/2015 |
| WO | WO2014033614 A1 | 3/2014 |

OTHER PUBLICATIONS

PCT International Search Report, International application No. PCT/EP2017/082444, dated Apr. 4, 2018.
(Continued)

*Primary Examiner* — Hoon K Song
(74) *Attorney, Agent, or Firm* — Larry Liberchuk

(57) ABSTRACT

Medical radiography requires specialist control of radiography equipment to achieve good imaging results. Typical errors that can occur consist of an inappropriate field of view being accidentally applied. This results in a "cropping effect" in which portions of the region of interest of a patient which would be of clinical use are omitted from the image. Conventionally, the only solution is to re-take the entire image with a more appropriate (and inevitably larger) field of view selected. This is undesirable, because it might require recall of the patient from another location, and the patient will be subject to two exposures, thus undesirably increasing their X-ray dosage. The present application proposes to use an anatomical atlas to analyse an X-ray image output from an initial exposure, in particular to assess whether significant anatomical elements are missing from the image. If elements are missing, the field of view of the X-ray imager is recalibrated, using collimation or pan/tilt adjustments, for example. A subsequent X-ray image is obtained, and combined with the initial image, to provide an output image. Because only a small area of the region of (Continued)

interest may subsequently need to be exposed, a smaller additional dose results.

13 Claims, 8 Drawing Sheets

(52) U.S. Cl.
CPC ............... *G06T 2207/20221* (2013.01); *G06T 2207/30061* (2013.01); *G06T 2207/30168* (2013.01)

(56) References Cited

OTHER PUBLICATIONS

Whaley, J. et al. "Investigation of the Variability in the Assessment of Digital Chest X-ray Image Quality", J Digit Imaging (2013), 26:217-226.

Taylor, N. et al., "The Art of Rejection: Comparative Analysis between Computed Radiography (CR) and Digital Radiography (DR) Workstations in the Accident & Emergency and General Radiology Departments at a District General Hospital Using Customised and Standardised Reject Criteria over a Three Year Period", Radiography, (2015) 21(3):236-241.

European Commission. European Guidelines on Quality Criteria for Diagnostic Radiographic Images. 1996.

Vik, T. et al., "A New Method for Robust Organ Positioning in CT Images", Proc ISBI 2012, p. 338, 2012.

\* cited by examiner

X-RAY APPARATUS HAVING A COMPOSITE FIELD OF VIEW

FIELD OF THE INVENTION

This invention relates generally to an apparatus for obtaining an X-ray image having a composite field of view. Also discussed is an X-ray imaging system, a method for obtaining an X-ray image having a composite field of view, a computer program element, and a computer-readable medium.

BACKGROUND OF THE INVENTION

The configuration of the field of view (FOV) for radiographic exposures such as lung radiographs, is a non-trivial task requiring the attention of a trained radiographer to operate an X-ray imager. A field of view which is set erroneously before an exposure means that a subsequent full X-ray image must be taken, because important anatomical detail could be missing from the first image. A patient might even need to be recalled for a second visit. Such occurrences are undesirable, leading to inefficiency in radiological departments, and leading to an increase in the X-ray dose absorbed by a patient. US 2015/0228071 A1 discusses an apparatus and method for automatically or semi-automatically controlling a collimator of an X-ray imager. However, such methods can be further improved.

SUMMARY OF THE INVENTION

Therefore, according to a first aspect, there is provided an apparatus for obtaining an X-ray image having a composite field of view. The apparatus comprises:

a processing unit.

The processing unit is configured to obtain first X-ray image data of a portion of a region of interest of an object using an X-ray imager, wherein the first X-ray image data is obtained from an X-ray imager having an adjustable field of view set to an initial field of view state, to compare the first X-ray image data to an anatomical model, to define a boundary error region contiguous to the first X-ray image data based on the comparison of the first X-ray image data to the anatomical model, to generate an updated field of view state based on the location of the boundary error region in the region of interest, to transmit the updated field of view state to an X-ray imager, to obtain second X-ray image data of the region of interest of the object using the X-ray imager when set to the updated field of view state, and to combine the first X-ray image data and the second X-ray image data to obtain an output image of the region of interest having a composite field of view.

Accordingly, an apparatus may be provided capable of controlling an X-ray imager which identifies an acquisition deficiency in a first X-ray image. Settings are generated which can be used to adjust the field of view of the X-ray imager, providing a further X-ray image which completes the imaging of the region of interest. The updated field of view may, for example, be smaller in area than the initial field of view. In this case, a patient would be subjected, upon the retake of the X-ray image, to a lower dose of X-ray radiation, compared to the first X-ray image exposure. Such an apparatus enables a reduction in the total X-ray dose delivered to a patient.

Optionally, in the apparatus according to the first aspect, the anatomical model comprises a probabilistic anatomical atlas representing a plurality of anatomical elements. The processing unit is further configured to compare portions of the first X-ray image to anatomical elements in the probabilistic anatomical atlas.

Accordingly, an accurate impression of a boundary error region in the first X-ray image may be derived to enable a second X-ray image to be obtained.

Optionally, in the apparatus according to first aspect, the processing unit is configured to identify an expected element, or portion of an expected element, in the anatomical model and/or probabilistic anatomical atlas, which is missing from the first X-ray image data. The processing unit is further configured to define a boundary error region in the X-ray image data based on an extrapolation of the anatomical model and/or probabilistic anatomical atlas out of the portion of the region of interest.

Accordingly, the extent of the error in the field of view of the first X-ray image may be identified using accurate anatomical data.

Optionally, the apparatus of the first aspect in which the processing unit is further configured to generate an image completion metric of the first X-ray image data based on a characteristic of the boundary error region. The second X-ray image data is obtained by the processing unit when the image completion metric surpasses an image completion condition.

Accordingly, for example, following a comparison with the anatomical model, it could be found that a lung element in the first X-ray image data is 95% complete, with only a small degree of the edge of a lung missing from the first X-ray image data. In this case, a second X-ray image would not be needed, thus saving the patient an unnecessary extra X-ray exposure.

Optionally, an apparatus according to the first aspect is provided, wherein the processing unit is further configured to combine the first X-ray image data and the second X-ray image data using an image stitching algorithm.

Thus, an image discontinuity between the first X-ray image data and the second X-ray image data in the image may be hidden from a medical professional.

Optionally, an apparatus according to the first aspect is provided, wherein the processing unit is configured to choose the updated field of view state to provide second X-ray image data which is contiguous to the first X-ray image data in the region of interest.

Accordingly, the updated field of view state provides an updated field of view which is as small as possible, because it does not overlap with the field of view of the first X-ray image data. Thus, exposure of the patient to unnecessary X-ray radiation may be further reduced.

Optionally, the apparatus according to the first aspect is provided, wherein the processing unit is configured to choose the updated field of view state to provide second X-ray image data which overlaps the first X-ray image data over at least a portion of the region of interest.

Accordingly, the second X-ray image data contains image information which, at least to an extent, is already present in the first X-ray image data. Thus, it is possible to combine the first X-ray image data and the second X-ray image data at a region of the image which is less relevant for forming a clinical diagnosis. For example, the overlap point could track down the spine of the patient, an area of the field of view which, in a specific patient imaging case, might not have relevance to a diagnosis of a disease mainly at the edges of the lobes of the lung, for example.

Optionally, the apparatus according the first aspect is provided, wherein the processing unit is further configured to identify an image combination region in the first X-ray image data using the anatomical model and/or the probabilistic anatomical atlas, to generate the updated field of view state based additionally on the image combination path, and wherein the first X-ray image data and the second X-ray image data are combined along the image combination region.

Accordingly, anatomical information provided a priori is used to define the updated field of view state, leading to a more accurate image combination region being defined.

Optionally, an apparatus according to the first aspect is provided with a processing unit which is further configured to add an artificial combination region marker to the output image, based on the initial and/or updated field of view state, wherein the combination region marker illustrates to a user possible regions of distortion in the output image.

Accordingly, an end user may be warned that regions of the composite output image are not suitable for forming a medical diagnosis.

Optionally, according to an apparatus of the first aspect, the processing unit is further configured to receive 3D optical image data of the object from a 3D camera, and wherein the initial and/or the updated field of view states are additionally based on the location of the object in the 3D optical image data.

Accordingly, initial or updated fields of view may be defined using the position of a patient in the field of view as captured by, for example, a camera. This enables the initial field of view to be set accurately, as well as the updated field of view, further reducing unnecessary X-ray exposure of the patient.

Optionally, the apparatus of the first aspect is provided, wherein the processing unit is further configured to receive a repeat exposure command from an input device, and wherein the processor is configured not to obtain the second X-ray image data until the repeat exposure command has been received from the input device.

Accordingly, the apparatus can be configured to wait for an operator command before activating an X-ray source which performs the second exposure of the patient, thus enhancing the safety of the apparatus.

Optionally, an apparatus is provided according to the first aspect, wherein the X-ray imager comprises an adjustable collimator, the initial field of view state comprises a first adjustable collimator setting, and wherein the processing unit is configured to generate the updated field of view state by using the processing unit to generate a second adjustable collimator position setting, and the processing unit is further configured to adjust the field of view of the X-ray imager by transmitting the second adjustable collimator position setting to the adjustable collimator of the X-ray imager.

Accordingly, X-ray collimator settings may be used to vary the field of view state.

According to a second aspect, an X-ray imaging system is provided.

The X-ray imaging system comprises:
an X-ray source having an adjustable field of view towards a target location;
an apparatus for obtaining an X-ray image having a composite field of view as claimed in the first aspect, or any of its optional embodiments, and
an X-ray detector arranged behind the target location to receive X-rays emitted from the X-ray source.

The X-ray imaging system is configured to provide a first X-ray image data to the apparatus, and the apparatus is configured to provide the updated field of view state to the X-ray source, to enable the field of view of the target location to be adjusted, and wherein the X-ray imaging system is configured to provide second X-ray image information to the apparatus for generating an X-ray image, which is configured to provide an output image of the region of interest having a composite field of view. Accordingly, the field of view of an X-ray imaging system may be automatically adjusted to capture elements of a region of interest of an imaged patient which were emitted from the first X-ray image.

According to a third aspect, a method for obtaining an X-ray image having a composite field of view is provided. The method comprises the steps of:
a) obtaining first X-ray image data of a portion of a region of interest of an object using an X-ray imager, wherein the X-ray image data is obtained using an X-ray imager having an adjustable field of view set to an initial field of view state;
b) comparing the X-ray image data to an anatomical model;
c) defining a boundary error region contiguous to the first X-ray image data based on the comparison of the first X-ray image data to the anatomical model;
d) generating an updated field of view state based on the location of the boundary error region in the region of interest;
e) transmitting the updated field of view state to an X-ray imager;
f) obtaining second X-ray image data of the region of interest of the object using the X-ray imager when set to the transmitted field of view state;
g) combining the first X-ray image data and the second X-ray image data to obtain an output image of the region of interest having a composite field of view.

Accordingly, a method is provided for generating an X-ray image which contains all of the relevant elements in a region of interest of a patient, with a lower amount of X-ray radiation exposure produced than would be the case if the field of view state of the second X-ray is set so as to encompass all relevant elements which were already encompassed within the first X-ray.

According to a fourth aspect, a computer program element is provided for controlling an apparatus and/or an X-ray system as described in the first or second aspects, which, when the computer program element is executed by the processor and/or system, is adapted to perform the method of the third aspect.

According to a fifth aspect, a computer-readable medium having stored the computer program element of the fourth aspect is provided.

In the following specification, the term "X-ray image data" refers to a data structure containing an array of pixels, wherein each pixel represents the intensity of a received X-ray at a specific pixel following the traversal of that X-ray through a region of interest of a patient. When assembled into a two-dimensional image, the intensity values provide an additive image representing the integral of the X-ray absorption at each pixel location.

In the following specification, the term "X-ray source" refers to an X-ray source containing, for example, a rotating anode X-ray tube. This emits X-ray radiation towards a region of interest of a patient to be imaged. The X-ray radiation traverses the patient at the region of interest, and is received by an X-ray detector, which may also be considered to be part of an X-ray imaging system. The X-ray imager may comprise automatically settable field of view parameters, such as, for example, an adjustable collimator arrangement, adjustable pan or tilt servomotors, adjustable height or x-y coordinate setting. In addition, the X-ray detector may be translated vertically or horizontally.

In the following specification, the term "field of view" refers to a portion of the region of interest that an X-ray imager may capture during a typical exposure. The field of view is generically defined by the distance of an X-ray imager from the X-ray detector and/or patient, and the size of the X-ray detector's aperture. The field of view may be translated across the region of interest by moving the X-ray imager in an x-z plane. The field of view may also be changed by panning or tilting the X-ray imager. The field of view may be cropped or enlarged by adjusting a collimator shutter, or shutters, of an X-ray source. Therefore, it will be appreciated that there are many ways to adjust the field of view of an X-ray imager.

In the following specification, the term "anatomical model" refers to a data structure, typically stored and executed on a processing means such as a computer. The anatomical model contains information defining the location and shape of common anatomical features of patients. A typical anatomical model defines a section of a generic patient body. The anatomical model contains a representation of structures such as lungs, rib bones, a spine, for example, and the likelihood that a certain anatomical element is present in a certain position. The anatomical model may be designed to allow anatomical elements to be identified from incomplete portions of an image of an organ.

The term "boundary error region" defines an unanatomical region in the X-ray image data. It will be appreciated that in this case of an incorrect collimation of the field of view, the boundary error region will appear to be cropped. For example, the extreme left or extreme right hand portions of a lung lobe may be missing from the X-ray image data. However, in this case of a field of view which is incorrectly set owing to a poor pan or tilt setting, a boundary error region may be defined by an anatomical element which is present, but warped, for example, into a "keystone shape". In other words, a boundary error region of the X-ray image data defines an area of the image which is not a faithful, or accurate reproduction of the anatomy of the patient.

Thus, it is a basic idea of the present specification to provide an automated method for robustly checking an initial X-ray image for problems with the field of view, automatically resetting the field of view to enable a second acquisition of anatomical regions not exposed within the initial exposure, and thereby to complete the full field of view using an image combination method. In this way, erroneous initial exposures may be utilized to complete a second exposure which has a smaller field of view, enabling a reduction in radiation exposure of a patient, compared to the radiation exposure that would be needed to undertake two complete images.

Although this application discusses the concept in terms of lung imaging based on the posterior-anterior view, it will be appreciated that the techniques discussed herein have wide applicability in radiography, wherever an initial X-ray image has missing boundary elements.

BRIEF DESCRIPTION OF THE DRAWINGS

Exemplary embodiments will be described with reference to the following drawings.

DETAILED DESCRIPTION OF EMBODIMENTS

Chest radiography is the most commonly performed clinical imaging examination, and plays an important role in detecting and diagnosing many diseases of the thoracic anatomy. The image quality is dependent on a wide range of specific individual factors such as the inclusion of the appropriate anatomy within the field of view, the contrast of structures of interest with respect to the background signal, as well as several aspects of the positioning of the patient's thorax with respect to the X-ray acquisition equipment.

The task of setting the field of view (FOV) for an exposure is conventionally performed by a radiographer. The patient is initially positioned in a region of interest in front of an X-ray detector. Then, a visible light, shining from within the tube-head of the X-ray equipment, and matching to the field of the X-ray radiation pattern, is used to establish the field of view on a patient's body. The height of the tube-head may firstly be varied, and then the height of a "bucky" containing the detector, and finally an adjustment may be made to the collimator opening, for example.

Figure 1:
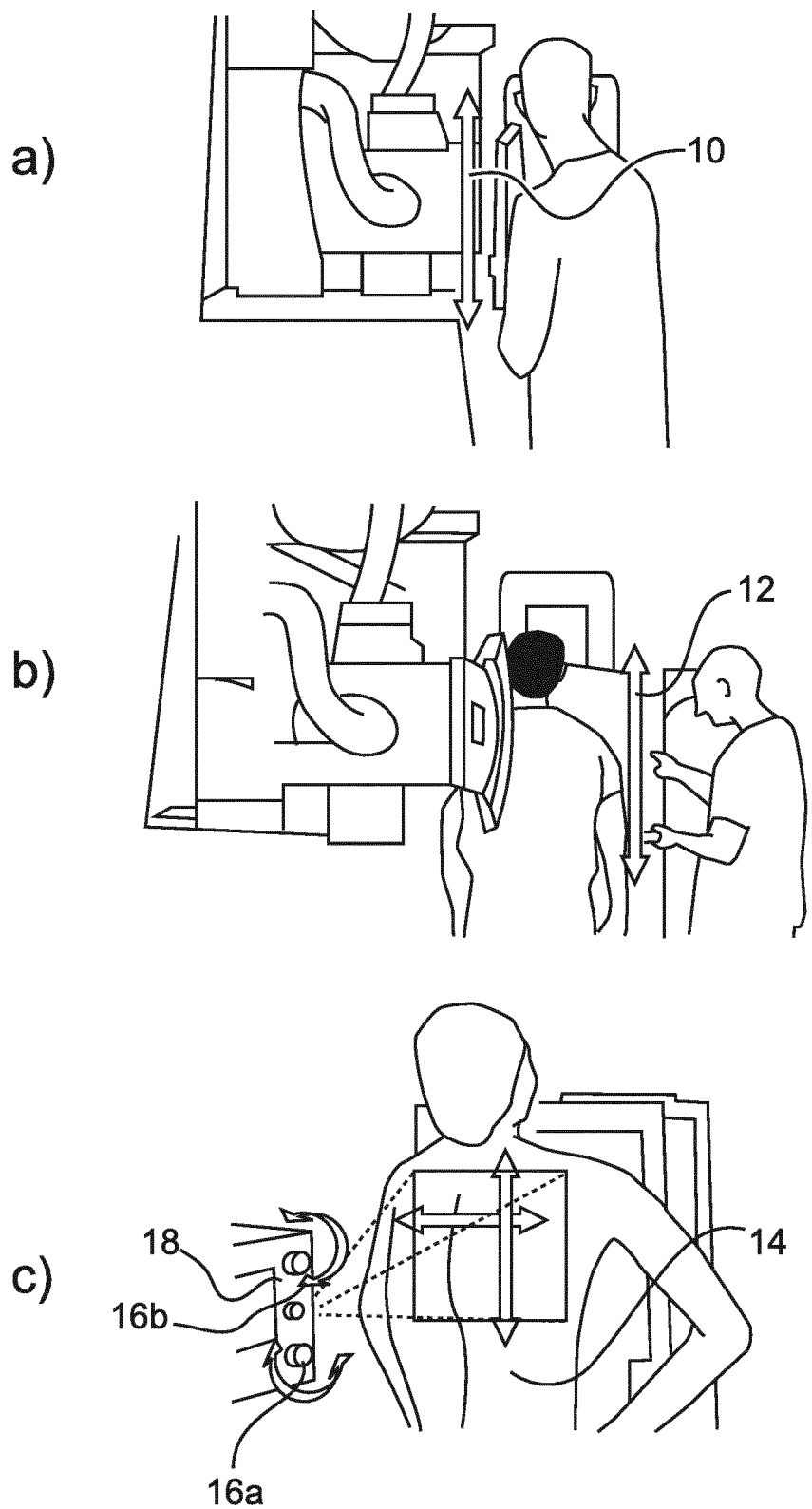
FIG. 1 illustrates a typical X-ray imaging scenario.

FIG. 1 shows a patient being examined in one of the most common projection geometries in clinical radiography, the posterior-anterior view of the chest. In FIG. 1, the X-ray source has been positioned such that the X-ray beams enter through the posterior of the chest, and exit the anterior of the chest, before reaching the X-ray detector. FIG. 1a) shows an operator adjusting the height 10 of the X-ray source. FIG. 1b) shows the operator adjusting the height 12 of the "bucky" containing the X-ray detector. FIG. 1c) shows the projection of a visible light collimation pattern 14 representing the field of view at a certain collimation state. The collimation pattern corresponds to the pattern of X-ray exposure when the X-ray exposure is in progress. Typically, the collimation pattern 14 is refined using controls 16a, 16b on an item of X-ray source control equipment 18. Varying the collimation pattern enlarges or shrinks the field of view of the system.

In clinical routine, aspects which determine the image quality are dependent to an extent upon the system operator's skill. Although standard operating procedures may be established by medical institutions, with an aim of ensuring a predefined minimum quality standard, enabling the minimization of common sources of potential error, opportunities for causing field of view errors still present themselves.

Setting the field of view of the X-ray equipment is an important part of an operator's task, but it is also a task which is prone to error. A common situation is "cut-off". This refers to an error in the setting of the field of view, whereby part of the anatomy of interest is, accidentally, not included within the X-ray image. Cut-off is one of the most common errors, and typically requires a retake of an entire X-ray image.

Figure 2:
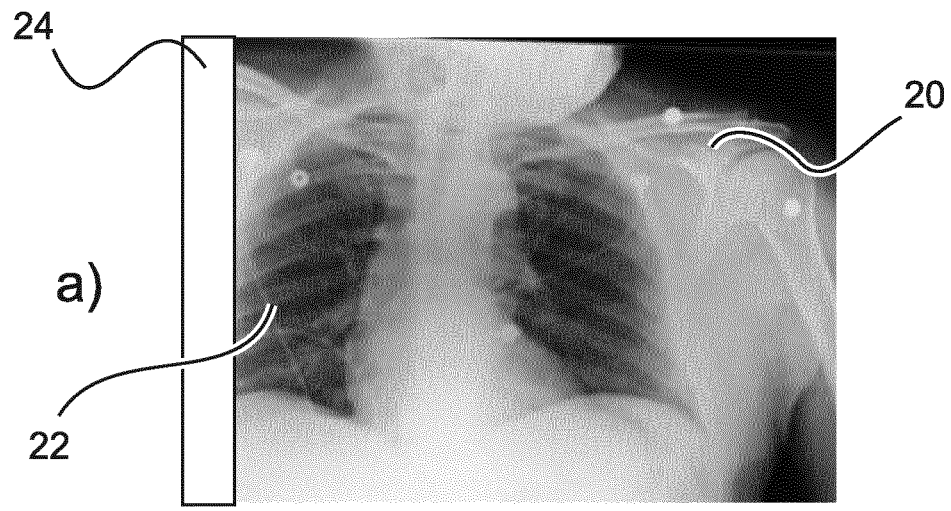
FIG. 2a) illustrates a first example image showing a cut-off lung in the field of view, due to an incorrect collimator setting.
FIG. 2b) shows a further example image showing a cut-off lung in the field of view, also due to an incorrect collimator setting.
Figure 2:
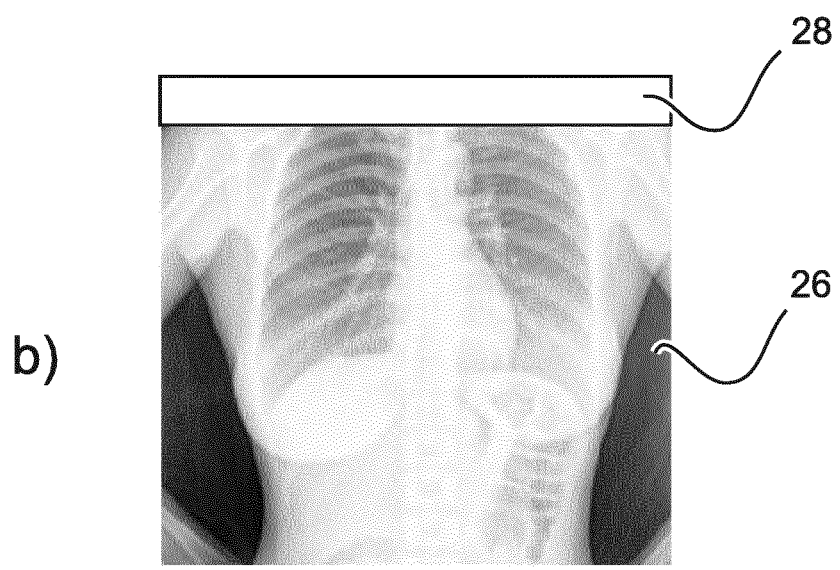

FIG. 2 shows two examples of cut-off.

In FIG. 2a), a posterior-anterior X-ray field of view 20 is shown in which a portion of a left lung lobe 22 has been cropped accidentally. Thus, a boundary error region could be considered to be defined, in an example, by the solid bar area 24.

Turning to FIG. 2b), the field of view 26 illustrates another posterior-anterior X-ray image. In this case, the field of view error occurs as a result of poor collimation of the top of the lung image, leading to a boundary error region 28 being observable, which should contain the top of the lung lobes.

Ordinarily, to obtain the full posterior-anterior lung image, the exposures of FIGS. 2a) and 2b) would need to be discarded. A completely new exposure would have to be made in each case. This is wasteful of X-ray facility time, and results in a patient receiving at least two times the required dose, compared to a case where the image had been taken correctly in one take. Thus, an approach for reducing such extra doses in response to field of view errors is required.

Figure 3:
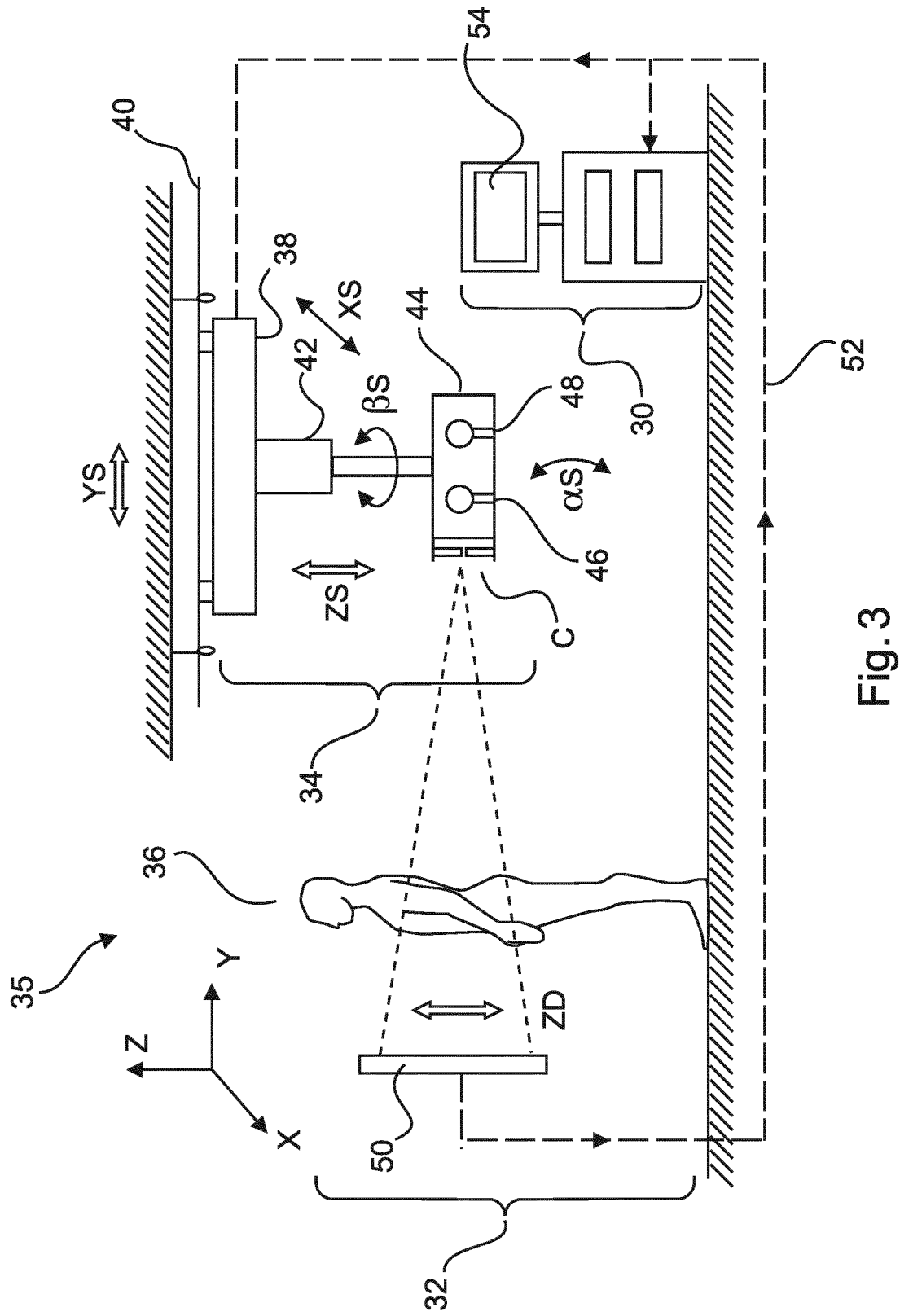
FIG. 3 shows an X-ray imaging system in accordance with the second aspect.

FIG. 3 shows an X-ray imaging system 35. The X-ray imaging system comprises a control apparatus 30, a detection assembly 31, and an X-ray imaging source assembly 34. A patient typically stands in the region of interest 36 in-between the X-ray source assembly 34 and the detection assembly 31.

FIG. 3 illustrates a patient in the posterior-anterior position. The X-ray imaging source assembly 34 comprises a roof-mounted dolly 38 configured to be suspended from a ceiling rail 40 of an X-ray imaging suite.

The X-ray imaging source assembly 34 is typically supported on the ceiling rail 40, enabling translational movement of the X-ray source towards or away from the patient (YS). The X-ray imaging source is suspended from the rail by a support member 42 which is movable in an up-down direction (towards and away from the floor, ZS axis), and also rotatable around the axis of the support member ($\beta$S).

An X-ray imaging source 44 is suspended from the support member 42 and comprises an enclosure containing an X-ray source 46 configured to emit X-ray radiation towards the region of interest 36, and a visible light source 48 configured to emit visible light towards the region of interest 36.

The X-ray source 46 is, for example, an rotating anode X-ray tube. The visible light source 48 is typically provided as an incandescent or an LED light. In-between the region of interest 36 and the X-ray source 46 and the visible light source 48 is a collimation element C.

The collimation element C is configured to shape the outer edges of the X-ray beam. A simple collimator comprises a shutter arranged to progressively cover the aperture of the X-ray imager. More sophisticated collimation elements comprise two shutters arranged in an orthogonal planar relationship to each other, enabling the size of the field of view to be altered. More complicated collimation arrangements include three-sided, four-sided, or "iris" collimator shutter arrangements.

Therefore, the collimation element C facilitates the definition of the outer extent of the field of view both of the X-ray radiation pattern and the visible light radiation pattern. It is noted also that the X-ray imaging source is tiltable by an angle $\alpha$S. The entire X-ray imaging arrangement may also be translated laterally (in FIG. 3, in a direction into, or out of, the page) through the XS dimension as shown on the drawing.

Thus, in the X-ray imaging system illustrated in FIG. 3, the field of view of the region of interest may be adjusted by manipulating the collimator element or elements C. It is, alternatively or in addition, possible to change the size of the field of view by advancing or retracting the X-ray imaging head in the YS direction. The field of view may be translated by adjusting the ZS and XS dimensions. Finally, the field of view may be reshaped by panning, or tilting, the X-ray imaging arrangement (BS, AS).

A field of view state comprising the aforementioned collimator and position settings is chosen by an operator, whilst illuminating the patient using the visible light source 48. Once satisfactory coverage of the region of interest has been provided, the X-ray source is activated, and the detector element 50 receives X-ray information about the region of interest 36. This is transmitted via data link 52 to the control arrangement 30. An operator may view the exposed X-ray image on an output device such as a monitor 54.

Thus, a conventional X-ray imaging system has been described. It will be appreciated that the field of view may be controlled using automatic servomotor to set the collimator, or X-ray imaging source position, for example.

Figure 4:
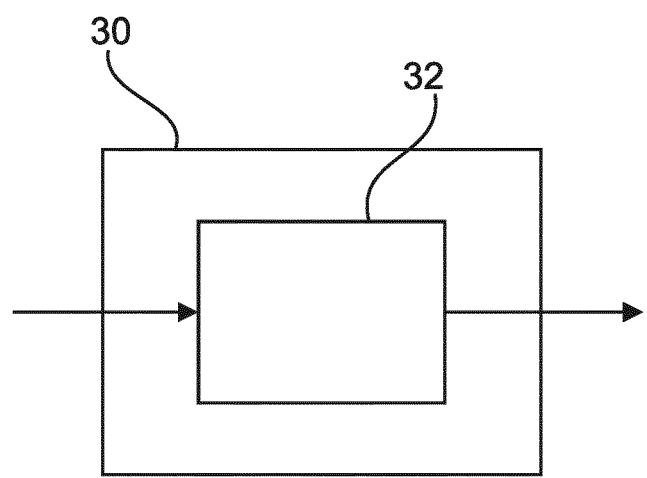
FIG. 4 shows an apparatus in accordance with the first aspect.

FIG. 4 shows an apparatus for obtaining an X-ray image having a composite field of view according to the first aspect. The apparatus comprises:

a processing unit 32.

The processing unit 32 is configured to obtain a first X-ray image data of a portion of a region of interest of an object using an X-ray imager 34, wherein the first X-ray image data is obtained from an X-ray imager 34 having an adjustable field of view set to an initial field of view state, to compare the first X-ray image data to an anatomical model, to define a boundary error region contiguous to the first X-ray image data based on the comparison of the first X-ray image data to the anatomical model, to generate an updated field of view state based on the location of the boundary error region in the region of interest, to transmit the updated field of view state to an X-ray imager, to obtain second X-ray image data of the region of interest of the object using the X-ray imager when set to the updated field of view state, and to combine the first X-ray image data and the second X-ray image data to obtain an output image of the region of interest having a composite field of view.

The apparatus may be implemented as a stand-alone module connectable to an existing X-ray imaging system using industry-standard remote operation protocols. In other words, the apparatus may, in an embodiment, be retrofittable to an existing system. Alternatively, the apparatus may be provided by updating the control software of an existing X-ray system. Alternatively, the apparatus may be provided as a module in a new X-ray system.

The apparatus may be configured to receive input image signals from the X-ray detector of an X-ray system, for example X-ray detector 50 in the system of FIG. 3.

The apparatus may also comprise an output interface to enable the processing unit 32 to control, or to adjust the field of view of an X-ray imaging system. For example, the apparatus 30 may comprise an output interface to control servomotors operative to adjust the tilt ($\alpha$S), the pan ($\beta$S), the height (ZS), the side displacement (XS), or the forward and backward displacement (YS), or the height of the X-ray detector (ZD).

Optionally, the boundary error region is generated by identifying a boundary in the first X-ray image data by fitting an anatomical element of the anatomical model to a matching element in the first X-ray image data. The boundary error region is identifiably from the region outside of the field of view of the first X-ray image, which the fitted anatomical element from the model extends into (the "boundary error area"). Optionally, the boundary error region can be generated by fitting a "bounding box" around the extent of the boundary error area. Of course, the foregoing discussion is one approach to generating the "boundary error region", but many others could be applied.

Optionally, the coordinates of the bounding box may be used to generate adjustable field of view settings, such as collimator position settings.

Optionally, the updated field of view state is generated by comparing coordinates of the boundary error region in the region of interest with coordinates of the aperture in the region of interest, resulting from the initial field of view state. A difference between the coordinates is computed. An updated field of view setting is calculated to transform the field of view such that it comprises at least the boundary error region.

In practice, there are many ways to accomplish this. Optionally, the coordinates of the boundary error region in the region of interest may be used directly to set a collimator for a second X-ray exposure. This approach results in minimal extra X-ray exposure to correct a cropping error. However, it would necessitate an image stitching line which might extend over a region of importance in the final image. Thus, optionally the coordinates of the boundary error region may be expanded into the field of view of the first X-ray image data by a quality margin, such as 5%, 10%, 15%, 20%, 25% of the width of the total region of interest. Setting the updated field of view additionally by generating commands to tilt, pan, or translate the X-ray source requires an additional lookup table, or optimization approach, for example, as known to the skilled person.

The apparatus 30 optionally comprises an interface to enable control of the visible light source 48 inside an X-ray source, or source control shutter. The apparatus 30 optionally comprises a control interface for controlling an adjustable collimator element C on an X-ray source 44.

Therefore, the apparatus 30 is able to interface with servomotors and/or actuators which are capable of adjusting the field of view of the X-ray system.

The processing unit 32 comprised in the apparatus 30 may be a conventional CPU processor, either dedicated to the task of the present aspect, or shared with a conventional operating system used to control an X-ray system. The apparatus may be a personal computer (PC).

The processing unit 32 may comprise multiple processors, for example simple tasks such as interfacing with the field of view control interfaces may be performed by a general purpose processor, and computationally intensive tasks such as comparing the X-ray image data to an anatomical model, may be performed by a graphics processing unit, a digital signal processor, or another form of accelerated processor.

The apparatus 30 may further comprise a data interface to enable provision of an anatomical model to the processing unit. For example, an anatomical model could be downloaded from a secure internet repository, a local hospital data repository, or the like. The anatomical model would be communicated to the apparatus 30 via a WLAN, LAN or PACS system. The anatomical model may be provided to the apparatus 30 by means of an external disc drive, a CD ROM, or a USB stick. Thus, it is possible to continuously update the anatomical model.

In operation, a patient is positioned in the field of view 36 of the X-ray system 35. Following an initial positioning of the patient in front of the X-ray detector 50, optionally using the light source 48 inside the X-ray source, a first X-ray image is obtained by exposing the patient 36 to X-ray radiation from the X-ray imaging source 44. The X-ray detector 50 detects the received intensity in a 2D area. The X-ray detector 50 transmits the detected data to the apparatus 30 using the data link 52. The first X-ray image is thus represented by first X-ray image data obtained in an initial field of view state of the X-ray system.

The processing unit 32 receives the first X-ray image data and compares the X-ray image data to an anatomical model.

It will be appreciated that many automated methods for the detection of relevant anatomy may be applied. A typical method applied is capable of identifying the selected anatomy, for example lung field boundaries, or parts of a selected anatomy, even when some elements of the anatomy being searched for are not present in the first X-ray image.

As an example, WO 2014/033614 A1 discusses an approach in which a probabilistic atlas of patient anatomy is used as a reference coordinate system. This enables the elements inside an X-ray field of view captured from the patient to be compared with the elements in the probabilistic atlas. Thus, anatomical elements present in the first X-ray image data may be matched and identified to elements within the probabilistic atlas.

Optionally, features detected within the field of view of the first X-ray image may be matched, even if the features in the first X-ray image data are incomplete owing to an error in the initial field of view state (caused, for example, by inappropriate collimation of the X-ray source).

This approach ensures a reliable and robust estimation of the field of view of the first X-ray image when provided with faulty images.

A comparison of the first X-ray image with the anatomical model (for example, the probabilistic atlas), enables deficiencies in the initial field of view state to be identified, and for an improved proposed field of view to be defined. Therefore, a boundary error region at an edge of the first X-ray image can be derived based on the comparison of the first X-ray image data to the anatomical model. The boundary error region represents, for example, a part of the image in which, or next to which, useful information is lacking. For example, the boundary error region could define the location at which a lung lobe is cut-off within the first image data.

In an example, the boundary error region is provided by the processor fitting a rectangular "bounding box" around an area in the anatomical model or probabilistic atlas which is not robustly matched in the first X-ray image data. The coordinates of the bounding box may be transposed into the coordinates of the field of view. Updated field of view parameters may then be generated.

The processing unit 32 generates an updated field of view state based on the location of the boundary error region in the region of interest. The updated field of view state reflects a changed extent of the field of view within the region of interest. The processing unit 32 represents the updated field of view state into updated parameters for setting the tilt ($\alpha$S), pan ($\beta$S), height (ZS), side translation (XS), forward and backward translation (YS), detector height (ZD), and collimation settings (C).

For example, these updated parameters may be generated based on a look-up table, or an interpolation function, between regions in the field of view which need to be covered in the second X-ray exposure, and settings for the tilt ($\alpha$S), pan ($\alpha$S), height (ZS), side translation (XS), forward and backward translation ($\beta$S), detector height (ZD), and collimation settings (C).

Optionally, only individual parameters are changed. For example, the updated field of view state can be generated based only on a change of the collimation elements C. The processing unit 32 then transmits the updated field of view state to the X-ray imaging system, for example the X-ray source 44 when the collimation element C needs to be changed. The processing unit 32 obtains a second X-ray image of the region of interest of the object using the X-ray imager when setting the updated field of view state.

The processing unit 32 completes an image processing operation by combining the first X-ray image data and the second X-ray image data to generate an image having a composite field of view owing to the combination of two separate X-ray images captured with different fields of view. For example, an image stitching algorithm may be used to combine the images.

Optionally, the generation of the updated field of view state comprises updating the position of the collimation elements C.

Optionally, the generation of the updated field of view state comprises performing an adjustment in the tilt of the X-ray source 44 (αS).

Optionally, the generation of an updated field of view state comprises altering the pan of the X-ray imaging source 44 (βS).

Optionally, the generation of an updated field of view state comprises altering the height of the X-ray imaging source 44 (ZS).

Optionally, the generation of an updated field of view state comprises adjusting the horizontal translation of the X-ray imaging source 44 (XS).

Optionally, the generation of an updated field of view state comprises adjusting the backward and forward position (YS) of the X-ray source 44.

Optionally, the generation of an updated field of view state comprises adjusting the height of the X-ray detector (ZD).

It will be appreciated that any combination of the previously listed sub-components of the field of view state may be adjusted by the processing unit 32, alone or in combination, to generate an updated field of view state.

Optionally, the collimator may have a single axis, and generating an updated field of view state comprises moving a single shutter to an updated position.

Optionally, the collimator element C comprises a two-axis collimator.

Optionally, the generation of the updated field of view state comprises generating an updated field of view state which encloses the boundary error region, such that the missing anatomy can be captured with a second X-ray image exposure.

Optionally, the generation of an updated field of view state comprises generating a field of view state which encloses the location of the boundary error region, and excludes a portion, or all, of the region of interest previously imaged by the X-ray imager when making the first X-ray image.

Therefore, the updated field of view state can be provided either to extend the first X-ray image only using a portion of the region of interest, or the X-ray image can be retaken over its entire extent, additionally including the missing area. Alternatively, a combination of approaches allows the X-ray image to be retaken including a missing portion, and a portion of the initially imaged area.

Figure 5:
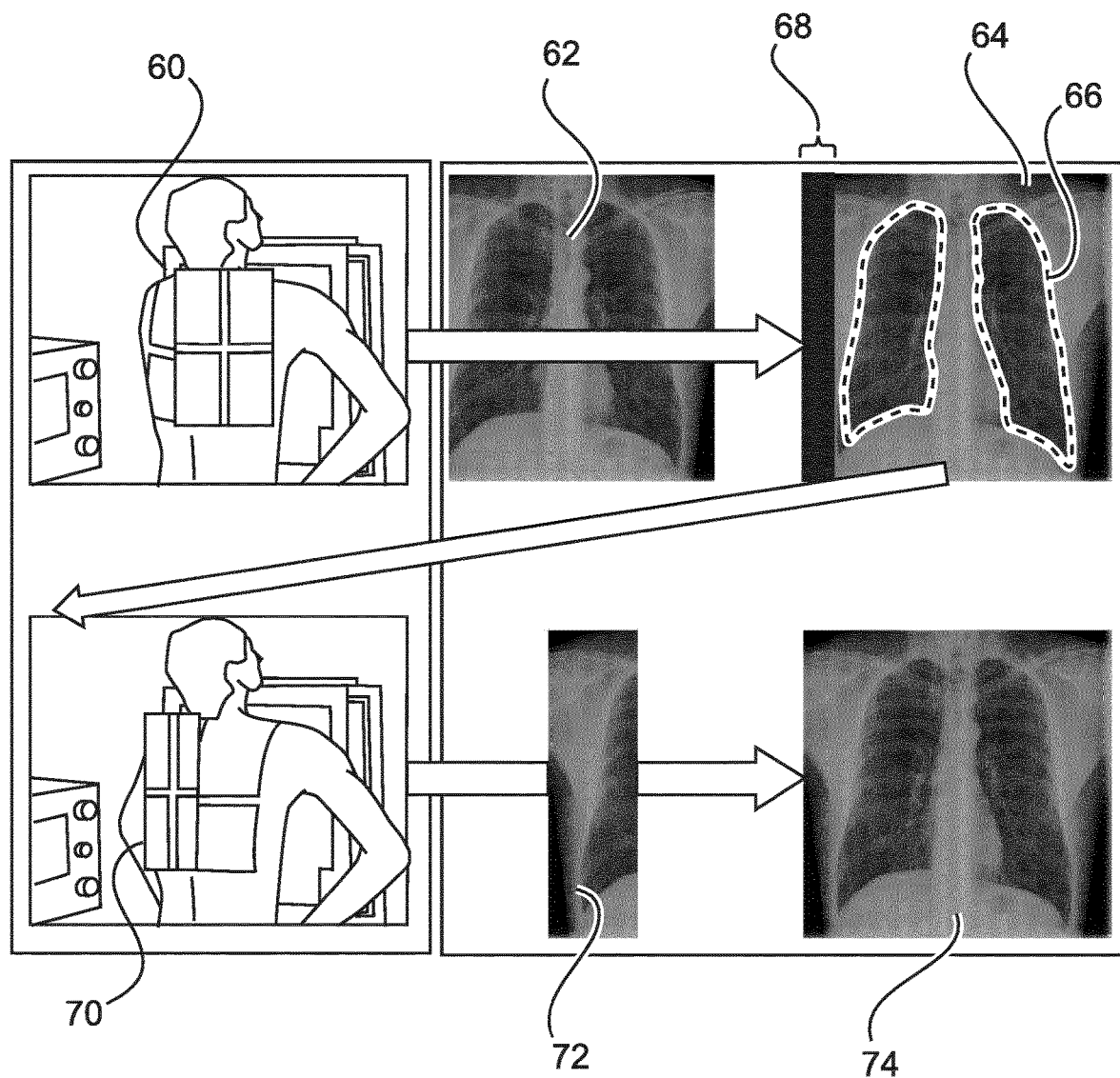
FIG. 5 shows a schematic view of a radiography workflow.

FIG. 5 provides an illustration of the acquisition of an X-ray image. It is seen that in a first stage 60, an initial collimation pattern is provided on the back of a patient in the posterior-anterior position. A first exposure 62 is obtained. The first exposure is obtained at an initial field of view state, for example initial collimation settings C. The first X-ray image 62 is compared, to an anatomical model, as shown in image 64. Image 64 shows that the dotted outline of a lung region 66 comprises a cut-off portion 68 representing a boundary error region. Because the location of the missing extent of the lung can be inferred from the anatomical model, an updated field of view state may be generated which extends over the boundary error region. The processing unit 32 updates the field of view state of the X-ray system at 70, and acquires a second X-ray image 72. The second X-ray image comprises the missing element of the lung anatomy. The image shown at 72 reflects the option discussed above, where the updated field of view captures only the missing data from the previous (first) X-ray image. However, the second X-ray image may also extend into the field of view of the first X-ray image.

Finally, image 74 represents a full field exposure provided after stitching together of the first X-ray image and the second X-ray image.

As illustrated in FIG. 5, a full field of view may be provided as a composite of two X-ray images, even when the field of view is initially erroneously set.

In other words, after acquisition of the first exposure, an automated check-up is performed for a detection of important anatomical features which are expected to be present in the image. If parts of the anatomy are missing, then the collimation elements, for example, of the X-ray source can be automatically repositioned, for example, and the operator can perform a second exposure in which only parts of the field of view which were accidentally not included in the first exposure are acquired. Finally, the images from the two exposures can be joined together to create a composite for field of view image.

Optionally, the anatomical model comprises a probabilistic anatomical atlas representing a plurality of anatomical elements, and the processing unit 32 is further configured to compare portions of the first X-ray image to anatomical elements in the probabilistic anatomical atlas.

Probabilistic anatomical atlases provide robust identification of anatomical elements, or missing anatomical elements.

Optionally, the processing unit 32 is further configured to identify an expected element, or portion of an expected element, in the anatomical model and/or probabilistic anatomical atlas, which is missing from the first X-ray image data, and wherein the processing unit 32 is further configured to determine a boundary error region in the first X-ray image data based on an extrapolation of the anatomical model and/or probabilistic anatomical atlas out of the portion of the region of interest.

In other words, once an expected element, or portion of an expected element, has been identified in the anatomical model and/or probabilistic anatomical atlas, the area of the region of interest which has been accidentally cropped out of the field of view by an inappropriate initial field of view state (such as an inappropriate collimation setting), can be defined with reference to the anatomical model and/or probabilistic anatomical atlas.

Optionally, the processing unit 32 is further configured to generate an image completion metric of the first X-ray image data based on a characteristic of the boundary error region, wherein the second X-ray image data is obtained by the processing unit when the image completion metric surpasses an image completion condition.

Accordingly, it might not be necessary to capture a second X-ray image, if the amount of the image missing in the boundary error region is marginal.

Optionally, the image completion condition could be defined as 99% of an anatomical element being present in the first X-ray image data, 95%, 90%, 85%, 80%, 75%, 70%, 65%, 60%, 55%, 50%, or the like. Alternatively, the image completion condition could use patient-specific data, in combination with the anatomical atlas. The image completion condition could be satisfied provided a patient-specific portion of the region of interest was included in the first X-ray image. The rules can be defined and configured in a user and/or institution-specific way to allow alternative rule-based configurations.

Optionally, the processing unit 32 is further configured to combine the first X-ray image data and the second X-ray image data using an image stitching algorithm. An image stitching algorithm would require the registration of the first X-ray image data to the second X-ray image data, calibration of the two images to each other, and then the blending of the two images.

Suitable image processing algorithms are known to the person skilled in the art for performing image stitching.

Accordingly, a composite field of view may be generated from the first X-ray image data and the second X-ray image data.

Optionally, the processing unit 32 is configured to choose the updated field of view state to provide second X-ray image data which is contiguous to the first X-ray image data in the region of interest.

Therefore, the first X-ray image data shares a common border with the second X-ray image data in the region of interest, but does not overlap. Therefore, unnecessary information which is already present in the first X-ray image is not duplicated in the second X-ray image, leading to a reduction in dose applied to the patient in this option.

Figure 6:
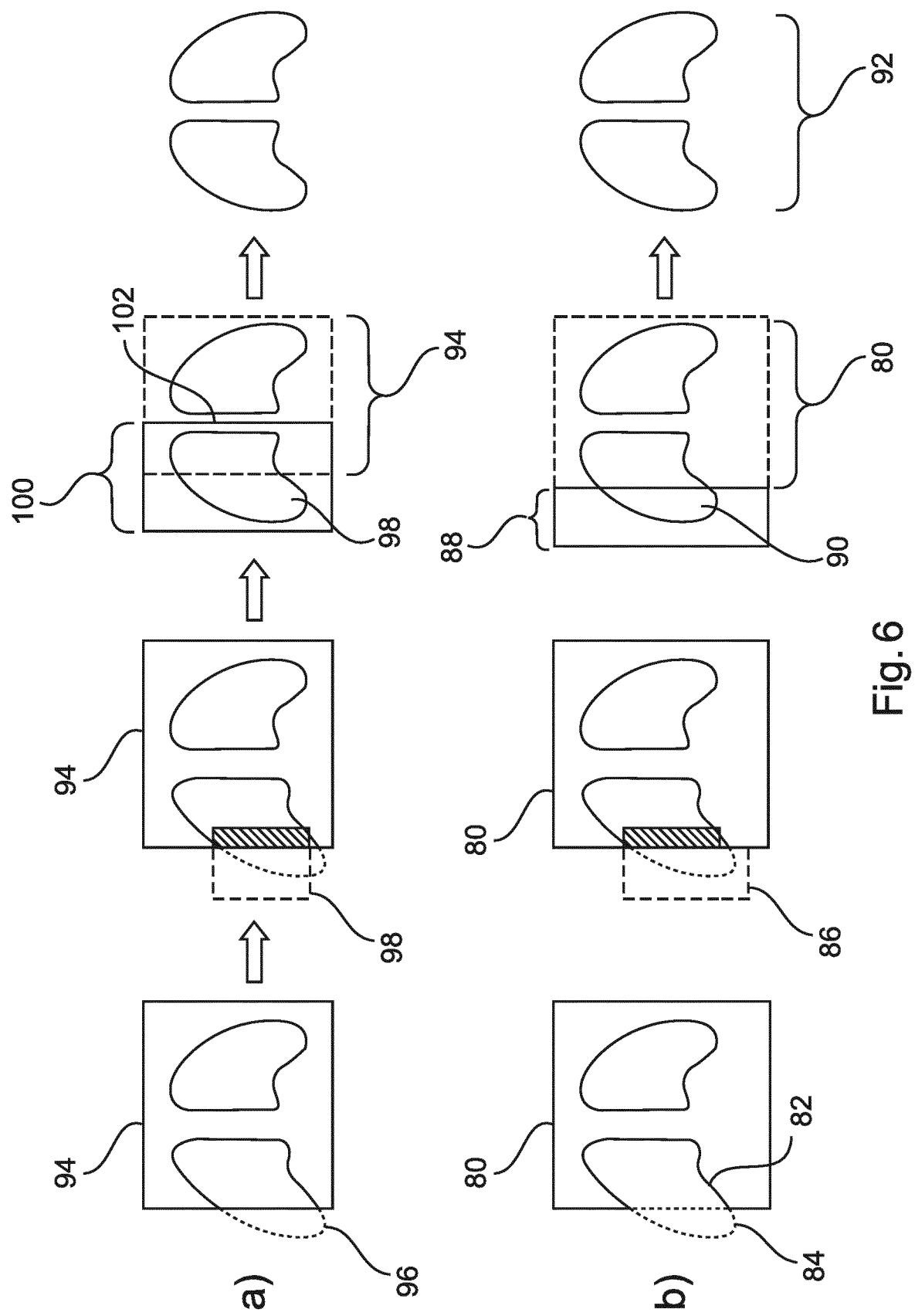
FIG. 6a) and FIG. 6b) show examples of collimation patterns according to embodiments discussed herein.

FIG. 6b) illustrates an assembly of a composite field of view according to the option discussed in the previous paragraph. In particular, the initial field of view 80 is seen to divide the left lung portion into a captured area 82 and an omitted area 84. Therefore, after comparison to an anatomical model, the boundary error region 86 is defined in a contiguous relationship to the initial field of view 80. This enables the updated field of view to be calculated, and for the collimation settings to be adjusted to provide an updated field of view 88, which encompasses the missing lung region 90. Following stitching of the images taken from the field of view 80 and the field of view 88, a composite image is provided 92. It is seen that the initial field of view 80 and the area covered by the updated field of view 88 are, in this option, exclusive to each other. This has the advantage of minimizing X-ray radiation exposure when performing a second exposure.

Optionally, the processing unit 32 is configured to choose the updated field of view state to provide second X-ray image data which overlaps the first X-ray image data over at least a portion of the region of interest.

It will be appreciated that if the initial field of view, and the boundary error region, interfere with a feature in the region of interest that is of clinical significance, it might not be beneficial to generate the second (updated) field of view at that boundary. Inevitably, some degradation occurs when using image stitching algorithms, and it would be preferable for this to be located away from any features of clinical interest.

Accordingly, FIG. 6a) shows an initial field of view 94 which omits a portion of a lung 96. As previously, it is determined using anatomical model that the portion of the lung 96 is missing from the initial field of view, and the boundary error region is defined as region 98 in the overall region of interest.

Either through an automated recognition that a feature at the boundary error region is of clinical interest, or using patient-specific data obtained by the processor 32, the updated field of view for obtaining the second X-ray image data is generated as region 100 of the overall region of interest. It is seen that region 100 partially overlaps with region 94. Therefore, the stitching boundary 102 lies down the central dividing line between the two lungs, and not in the region of the left lung lobe in the boundary error region 98. This is advantageous, if for example, a clinical pathology is present in the boundary error region which must be securely identified. It will be appreciated that this approach leads to a slightly higher patient X-ray dose, but providing the benefit of a clearer X-ray image.

The decision as to whether or not to provide a contiguous field of view in the update, or an overlapping updated field of view, may be semi-automated, or automated, based on an anatomical model or probabilistic atlas.

Figure 7:
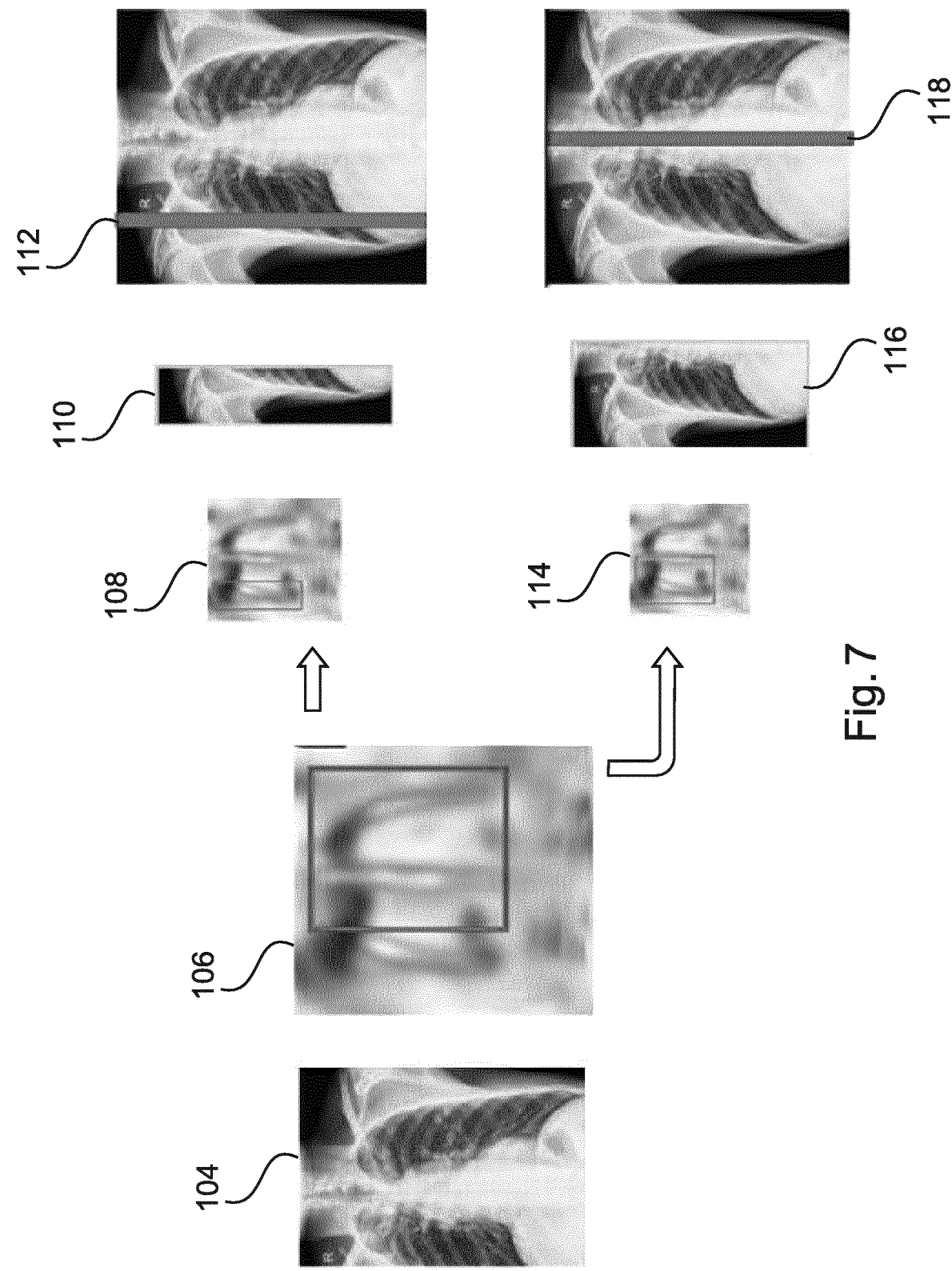
FIG. 7 shows an examples of image stitching options following different collimation approaches.
Figure 8:
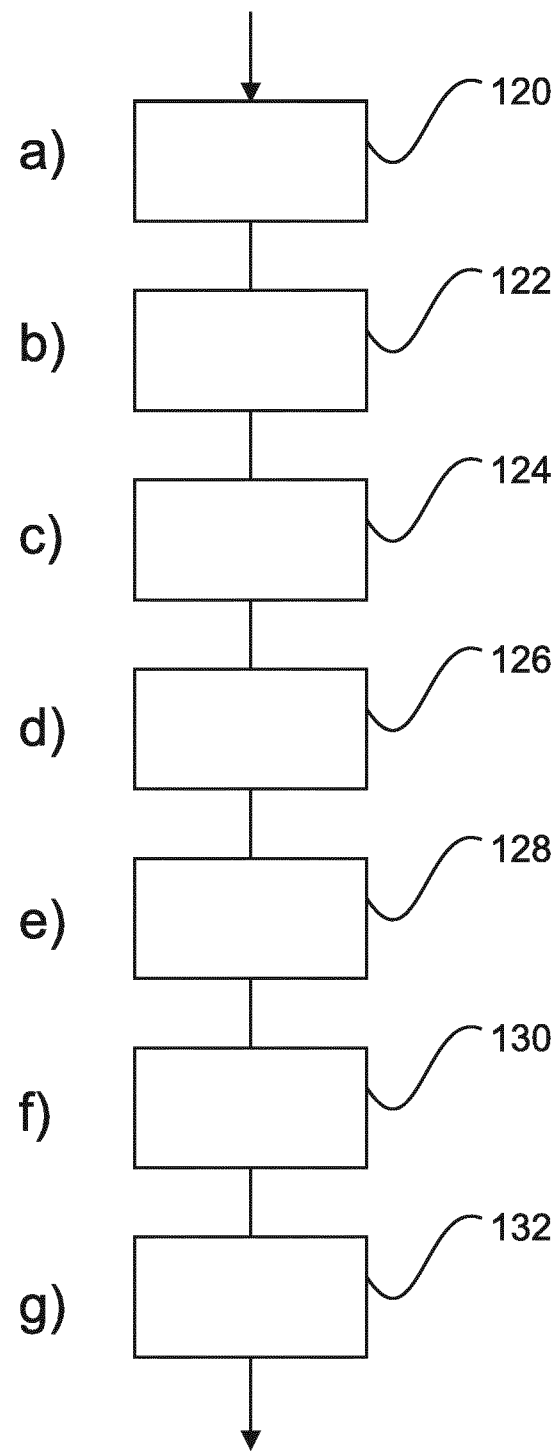
FIG. 8 shows a method in accordance with the third aspect.

FIG. 7 indicates a first exposure 104 having a collimation error. The field of view of the first exposure 104 is matched using a probabilistic atlas model 106. The probabilistic atlas model provides a plurality of options about how to configure the field of view for a subsequent exposure. In a first option 108, a field of view is chosen leading to a contiguous image 110 which may be stitched with a line running through the lung lobe itself 112. Alternatively, a second option 114 is provided resulting in an overlapping image in the overall region of interest 116, resulting in an image stitching line 118 running substantially in the spinal area of the region of interest.

Of course, the field of view completion decision engine may provide more than two field of view options. The field of view completion decision engine may use any of the degrees of freedom of the field of view discussed previously. The field of view completion decision engine may be configured to trade-off the exposure to additional X-ray dose, with an optimal image stitching location.

Optionally, the field of view completion decision engine may be configured to receive patient-specific data to enable a join line 112 or 118 to be placed in a suitable location of the image.

Optionally, the processing unit 32 is further configured to identify an image combination region in the first X-ray image data using the anatomical model and/or the probabilistic anatomical atlas, to generate the updated field of view state based additionally on the image combination region, and the first X-ray image data and the second X-ray image data are combined along the image combination region.

Optionally, the processing unit 32 is further configured to add an artificial combination region marker to the output image based on the initial and/or updated field of view state, wherein the combination region marker illustrates to a user possible regions of distortion in the output image.

Accordingly, it is possible to warn a user that a particular region of an image has been generated from a composite of two fields of view, enabling the medical professional to treat the information from that part of the image with more care.

It will be appreciated that the artificial combination region marker may be implemented, for example, as a semi-transparent bar region, or discoloured region in the output image. Additionally, the combination region marker may be provided with a dotted line, or a text annotation in the output image.

Optionally, the processing unit 32 is further configured to receive 3D optical image data of the object from a 3D camera, and the initial and/or the updated field of view states are additionally based on the location of the object in the 3D optical image data.

An extension of the proposed approach combines techniques for field of view setting, such as collimation setting, based upon optical sensing of the patient surface. Such approaches are discussed in WO 2014/033614 A1. Such approaches using optical field of view setting enable localization of the field of view settings based upon an optical assessment (by automated analysis of a video, or photograph) of the patient. However, an optical assessment of the patient only defines the external surface of the patient, and it is frequently not possible to fully estimate the location of the lungs, for example, since lung size is not fully determinable by the location of the patient surface. Thus, patients with different physiological conditions can have significant variations in the extent and positioning of the lungs within the body. If such an automated system determines an erroneous over-field of view correction (such as over-collimation), the present approach would enable the provision of a second exposure, before the patient has re-positioned away from the X-ray detector.

Optionally, the processing unit 32 is further configured to receive a repeat exposure command from an input device, and the processor is configured not to obtain the second X-ray image data until the repeat exposure command has been received from the input device.

The operator still plays a significant role in the proposed approach, and will often be required by regulatory consideration to evaluate and to confirm the updated field of view settings.

Optionally, the updated field of view settings can be provided to the operator by a visual feedback provided by a light-guide in an X-ray imaging system. Then, the operator authorizes the second exposure using the input device. This enhances the safety of the proposed approach.

Optionally, the X-ray imager 44 comprises an adjustable collimator, the initial field of view state comprises a first adjustable collimator setting, and the processing unit 32 is configured to generate the updated field of view state by using the processing unit to generate a second adjustable collimator position setting, and the processing unit 32 is further configured to adjust the field of view of the X-ray imager by transmitting the second adjustable collimator position setting to the adjustable collimator of the X-ray imager.

According to a second aspect of the invention, there is provided an X-ray imaging system 35. The X-ray imaging system 35 comprises
  an X-ray source 44 having an adjustable field of view towards a target location 36,
  an apparatus 30 for generating an X-ray image having a composite field of view as claimed in one of the previous aspects or options, and
  an X-ray detector 50 arranged behind the target location 36 to receive X-rays emitted from the X-ray source.

The X-ray imaging system 35 is configured to provide first X-ray image data to the apparatus 30, and the apparatus 30 is configured to provide the updated field of view state to the X-ray source 44 to enable the field of view of the target location to be adjusted, and wherein the X-ray imaging system is configured to provide second X-ray image information to the apparatus 30 for generating an X-ray image, which is configured to provide an output image of the region of interest having a composite field of view.

Optionally, the X-ray system 35 further comprises an output viewing means 54, such as a computer monitor operatively connected to the apparatus 30. This enables the viewing of first X-ray data and second X-ray data.

According to a third aspect of the invention, there is provided a method for obtaining an X-ray image having a composite field of view. The method comprises:
a) obtaining 120 first X-ray image data of a portion of a region of interest of an object using an X-ray imager, wherein the first X-ray image data is obtained using an X-ray imager having an adjustable field of view set to an initial field of view state;
b) comparing 122 the first X-ray image data to an anatomical model;
c) defining 124 a boundary error region contiguous to the first X-ray image data based on the comparison of the first X-ray image data to the anatomical model;
d) generating 126 an updated field of view state based on the location of the boundary error region in the region of interest;
e) transmitting 128 the updated field of view state to an X-ray imager;
f) obtaining 130 second X-ray image data of the region of interest of the object using the X-ray imager when set to the transmitted updated field of view state;
g) combining 132 the first X-ray image data and the second X-ray image data to obtain an output image of the region of interest having a composite field of view.

Optionally, the method of the third aspect is provided wherein the anatomical model comprises a probabilistic anatomical atlas representing a plurality of anatomical elements, and step b) further comprises:
b1) comparing portions of the first X-ray image to anatomical elements in the probabilistic anatomical atlas.

Optionally, the method of the third aspect further comprises:
b2) identifying an expected element, or portion of an element, in the anatomical model and/or probabilistic anatomical atlas which is missing from the first X-ray image data, and wherein in step c), the boundary error region in the first X-ray image data is defined based on an extrapolation of the anatomical model and/or probabilistic anatomical atlas out of the portion of the region of interest.

Optionally, the method of the third aspect further comprises:
c1) generating an image completion metric of the first X-ray image data based on a characteristic of the boundary error region; and wherein, in step f), the second X-ray image data is obtained when the image completion metric surpasses an image completion condition.

Optionally, the method of the third aspect is provided, wherein in step g), the first X-ray image data and the second X-ray image data are combined using an image stitching algorithm.

Optionally, the method of the third aspect is provided, wherein the updated imager collimator setting is chosen to provide second X-ray image data which is contiguous to the first X-ray image data in the region of interest.

Optionally, the method of the third aspect is provided, wherein the updated imager collimator setting is chosen to provide second X-ray image data which overlaps the first X-ray image data over at least a portion of the region of interest.

Optionally, the method of the third aspect further comprises
c2) identifying an image combination path in the first X-ray image data using the anatomical model and/or the probabilistic anatomical atlas;

d1) generating the updated imager collimator setting based additionally on the image combination path; and
wherein in step G), the first X-ray image data and the second X-ray image data are combined along the image combination path.

Optionally, the method of the third aspect further comprises:
g1) adding an artificial combination region marker to the output image based on the initial and/or updated collimator setting, wherein the combination region marker illustrates to a user possible regions of distortions in the output image.

Optionally, the method of the third aspect further comprises:
a1) receiving 3D optical image data of the object from a 3D camera; and wherein the initial and/or the updated collimator settings are additionally based on the location of the object in the 3D optical image data.

Optionally, the method of the third aspect further comprises:
h) displaying the output image to a user.

Optionally, the method of the third aspect further comprises:
e1) receiving a "repeat exposure" command from a user, and wherein step f) is not performed until the "repeat exposure" command has been received from the user.

According to a fourth aspect, there is provided a computer program element for controlling a processing unit and/or X-ray system as discussed in the first or second aspects, which, when the computer program element is executed by the processing unit and/or system, is adapted to perform the method of the second aspect.

According to a fifth aspect, there is provided a computer-readable medium having stored the computer program element discussed in the fourth aspect. In another aspect, a computer program, or a computer program element, is provided that is characterized by being adapted to execute the method steps of the method of the second aspect, or its embodiments, as discussed according to one of the preceding embodiments, on an appropriate system.

The computer program element might therefore be stored on computer units, which might also be part of an embodiment. This computing unit may be adapted to perform or induce the performance of the steps described above. Moreover, it may be adapted to operate the components of the above-described apparatus. The computing unit can be adapted to operate automatically, and/or to execute the orders of a user. A computing program may be loaded into the working memory of a data processor. The data processor may, thus, be equipped to carry out the method of the second aspect.

This exemplary embodiment covers both the computer program which is configured to use the invention initially, or a computer program that is configured from an existing program into a program that uses the invention by means of a software update, for example.

The computer program element is thus able to provide all necessary steps necessary to fulfil the procedure required according to the second aspect discussed above. According to a further exemplary embodiment of the present invention, a computer-readable medium, such as a CD-ROM, is presented. The computer-readable medium has a computer-readable medium with a computer program element stored on it, wherein the computer program element is described in the previous section.

A computer program may be stored and/or distributed on a suitable medium, such as an optical storage medium or a solid-state medium supplied together with, or is part of the hardware. The computer-readable medium may also be distributed in other forms, such as via the Internet, or via other wired or wireless telecommunication systems.

The computer program can also be presented over a network, like the World Wide Web, and can be downloaded into the working memory of a data processor from such a network. According to a further exemplary embodiment of aspects of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type features, whereas other embodiments are described with respect to apparatus-type features. A person skilled in the art will gather from the above, and the following description that, unless otherwise notified, in addition to any combination of features belonging to one type of subject-matter, also any other combination of features belonging to one type of subject-matter, is considered to be disclosed within this application. All features can be combined to provide a synergetic effect which is more than the simple summation of the features.

Whilst the invention has been illustrated and described in detail in the drawings and in the foregoing description, such illustration and description are to be considered to be illustrative or exemplary, and not restrictive. The invention is not limited to the disclosed embodiments.

Other variations to the disclosed embodiments can be understood, and effected, by those skilled in the art in practicing the claimed invention, from a study of the disclosure and the drawings, the description, and the dependent claims.

In the claims, the word "comprising" does not exclude other elements or steps. The indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope of the claims.

The invention claimed is:

1. An apparatus for obtaining an X-ray image having a composite field of view, comprising:
   an X-ray imager; and
   a processor configured to:
      obtain first X-ray image data of a portion of a region of interest of an object using the X-ray imager, wherein the first X-ray image data is obtained from the X-ray imager having an adjustable field of view set to an initial field of view state;
      compare the first X-ray image data to an anatomical model, wherein the anatomical model comprises a probabilistic anatomical atlas representing a plurality of anatomical elements, and wherein the comparing includes a comparison between portions of the first X-ray image and anatomical elements in the probabilistic anatomical atlas;
      define a two or more dimensional region as a boundary error region contiguous to the first X-ray image data based on the comparison between the portions of the first X-ray image data and the anatomical elements in the probabilistic anatomical atlas;

generate an updated field of view state based on a location of the two or more dimensional region being the boundary error region in the region of interest;
transmit the updated field of view state to an X-ray imager;
obtain second X-ray image data of the region of interest of the object using the X-ray imager set to the updated field of view state; and
combine the first X-ray image data and the second X-ray image data to obtain an output image of the region of interest having a composite field of view.

2. The apparatus of claim 1, wherein the processor is further configured to:
identify an expected element, or portion of an expected element, in the anatomical model and/or probabilistic anatomical atlas, which is missing from the first X-ray image data, and
define the boundary error region in the first X-ray image data based on an extrapolation of the anatomical model and/or probabilistic anatomical atlas out of the portion of the region of interest.

3. The apparatus according to claim 1,
wherein the processor is further configured to generate an image completion metric of the first X-ray image data based on a characteristic of the boundary error region, wherein the second X-ray image data is obtained by the processor when the image completion metric surpasses an image completion condition.

4. The apparatus according to claim 1, wherein the processor is further configured to combine the first X-ray image data and the second X-ray image data using an image stitching algorithm.

5. The apparatus according to claim 1, wherein the processor is configured to choose the updated field of view state to provide second X-ray image data which is contiguous to the first X-ray image data in the region of interest.

6. The apparatus according to claim 1, wherein the processor is configured to choose the updated field of view state to provide second X-ray image data which overlaps the first X-ray image data over at least a portion of the region of interest.

7. The apparatus according to claim 6, wherein the processor is further configured to:
identify an image combination region in the first X-ray image data using the anatomical model and/or the probabilistic anatomical atlas; and
generate the updated field of view state based additionally on the image combination region, wherein the first X-ray image data and the second X-ray image data are combined along the image combination region.

8. The apparatus according to claim 1, wherein the processor is further configured to add an artificial combination region marker to the output image based on the initial and/or updated field of view state, wherein the combination region marker illustrates possible regions of distortion in the output image.

9. The apparatus according to claim 1, wherein the processor is further configured to receive a repeat exposure command from an input device, and not to obtain the second X-ray image data until the repeat exposure command has been received from the input device.

10. The apparatus according to claim 1, wherein the X-ray imager comprises an adjustable collimator, wherein the initial field of view state comprises a first adjustable collimator setting, wherein the processor is configured to generate the updated field of view state by generating a second collimator position setting, and wherein the processor is further configured to adjust the field of view of the X-ray imager by transmitting the second collimator position setting to the adjustable collimator of the X-ray imager.

11. An X-ray imaging system, comprising:
an X-ray source having an adjustable field of view towards a target location;
an apparatus for obtaining an X-ray image having a composite field of view as claimed in claim 1; and
an X-ray detector arranged behind the target location to receive X-rays emitted from the X-ray source.

12. A method for obtaining an X-ray image having a composite field of view, comprising:
obtaining first X-ray image data of a portion of a region of interest of an object using an X-ray imager, wherein the first X-ray image data is obtained using an X-ray imager having an adjustable field of view set to an initial field of view state;
providing a comparison between the first X-ray image data and an anatomical model, wherein the anatomical model comprises a probabilistic anatomical atlas representing a plurality of anatomical elements, and wherein the comparison includes a comparison between portions of the first X-ray image and anatomical elements in the probabilistic anatomical atlas;
defining a two or more dimensional region as a boundary error region contiguous to the first X-ray image data based on the comparison between the portions of the first X-ray image data and the anatomical elements in the probabilistic anatomical atlas;
generating an updated field of view state based on a location of the two or more dimensional region being the boundary error region in the region of interest;
transmitting the updated field of view state to the X-ray imager;
obtaining second X-ray image data of the region of interest of the object using the X-ray imager when set to the transmitted field of view state; and
combining the first X-ray image data and the second X-ray image data to obtain an output image of the region of interest having a composite field of view.

13. A non-transitory computer-readable medium having one or more executable instructions stored thereon, which, when executed by a processor, cause the processor to perform a method for obtaining an X-ray image having a composite field of view, the method comprising:
obtaining first X-ray image data of a portion of a region of interest of an object using an X-ray imager, wherein the first X-ray image data is obtained using an X-ray imager having an adjustable field of view set to an initial field of view state;
providing a comparison between the first X-ray image data and an anatomical model, wherein the anatomical model comprises a probabilistic anatomical atlas representing a plurality of anatomical elements, and wherein the comparison includes a comparison between portions of the first X-ray image and anatomical elements in the probabilistic anatomical atlas;
defining a two or more dimensional region as a boundary error region contiguous to the first X-ray image data based on the comparison between the portions of the first X-ray image data and the anatomical elements in the probabilistic anatomical atlas;
generating an updated field of view state based on a location of the two or more dimensional region being the boundary error region in the region of interest;
transmitting the updated field of view state to the X-ray imager;

obtaining second X-ray image data of the region of interest of the object using the X-ray imager when set to the transmitted field of view state; and combining the first X-ray image data and the second X-ray image data to obtain an output image of the region of interest having a composite field of view.

\* \* \* \* \*